United States Patent [19]
Wojciechowski et al.

[11] Patent Number: 5,340,745
[45] Date of Patent: Aug. 23, 1994

[54] TEMPERATURE SCANNING REACTION METHOD

[75] Inventors: Bohdan W. Wojciechowski; Norman M. Rice, both of Kingston, Canada

[73] Assignee: Queen's University, Kingston, Canada

[21] Appl. No.: 51,413

[22] Filed: Apr. 23, 1993

Related U.S. Application Data

[63] Continuation-in-part of Ser. No. 833,182, Feb. 10, 1992, abandoned.

[51] Int. Cl.$^5$ ............................................. G01N 31/10
[52] U.S. Cl. ..................................... 436/34; 422/99; 422/130; 436/147
[58] Field of Search .................... 436/34, 147; 422/99, 422/130

[56] References Cited

U.S. PATENT DOCUMENTS 3,578,404  5/1971  Walles et al. ..................... 436/34
4,667,730  5/1987  Zemp ............................. 422/138 X Primary Examiner—Jill A. Johnston
Attorney, Agent, or Firm—Richard J. Hicks

[57] ABSTRACT

A method for rapidly collecting kinetic rate data from a temperature scanning reactor for chemical reactions. The method, which is particularly useful for studying catalytic reactions, involves ramping (scanning) of the input temperature to a reactor and recording of output conversion and bed temperature without waiting for isothermal steady state to be established.

4 Claims, 9 Drawing Sheets

CONVERSION VS TEMPERATURE

CONVERSION VS INLET TEMPERATURE

OUTLET TEMPERATURE (K)
CONVERSION VS OUTLET TEMPERATURE

CONVERSION VS TEMPERATURE

OUTLET TEMPERATURE VS INLET TEMPERATURE

TEMPERATURE VS TEMPERATURE
CONVERSION VS TEMPERATURE

TEMPERATURE SCANNING REACTION METHOD

CROSS REFERENCE TO RELATED APPLICATION

This application is a continuation-in-part of our earlier filed U.S. patent application Ser. No. 07/833,182 filed Feb. 10, 1992, now abandoned.

FIELD OF THE INVENTION

This invention relates to a method and apparatus for determining rates of reaction in a chemical reactor system.

BACKGROUND OF THE INVENTION

The acquisition of kinetic data from a chemical reaction system is usually a laborious, time consuming and expensive undertaking. As a consequence, evaluation of catalysts and reaction conditions, in the chemical industry, for example, is often carried out with scanty data which does not allow for a full understanding of the system under study. Conventional methods generally include collecting iso-thermal conversion data at steady state for a number of feed rates. Because of operating requirements, such as waiting for steady state, start-up, shutdown etc., it is usually only possible to make 1-5 runs per day in any given system. At least 30 runs are needed over a range of 3 or 4 temperatures. About 8-10 space velocities are required at each temperature, and hence it will be seen that such a study will take about two months to complete. This time period may be considerably increased if repeat runs are required to verify catalyst stability over this length of time or to obtain a statistical measure of variance or if feed composition of reactant concentration are to be varied. Frequently, therefore, there may be as much as one person-year required for a full research study. There is, therefore, a considerable need for an improved method of acquiring kinetic rate data for chemical reactors.

OBJECT OF INVENTION

An object of the present invention is to provide a method for determining kinetic rate data for chemical reactors which is at least an order of magnitude faster than conventional methods.

BRIEF STATEMENT OF INVENTION

Thus, by one aspect of this invention there is provided a method for rapid collection of kinetic rate data from a temperature scanning reactor in which a feed stock is reacted under non-steady state conditions to form a conversion product comprising,
ramping the input temperature of said feed stock rapidly over a selected range of temperature,
continuously monitoring output conversion and output temperature while ramping the input temperature and determining a rate of reaction representative of steady state conditions from input and output temperature and output conversion data obtained during said non-steady state operation of the reactor.

DETAILED DESCRIPTION OF A PREFERRED EMBODIMENTS

Figure 1:
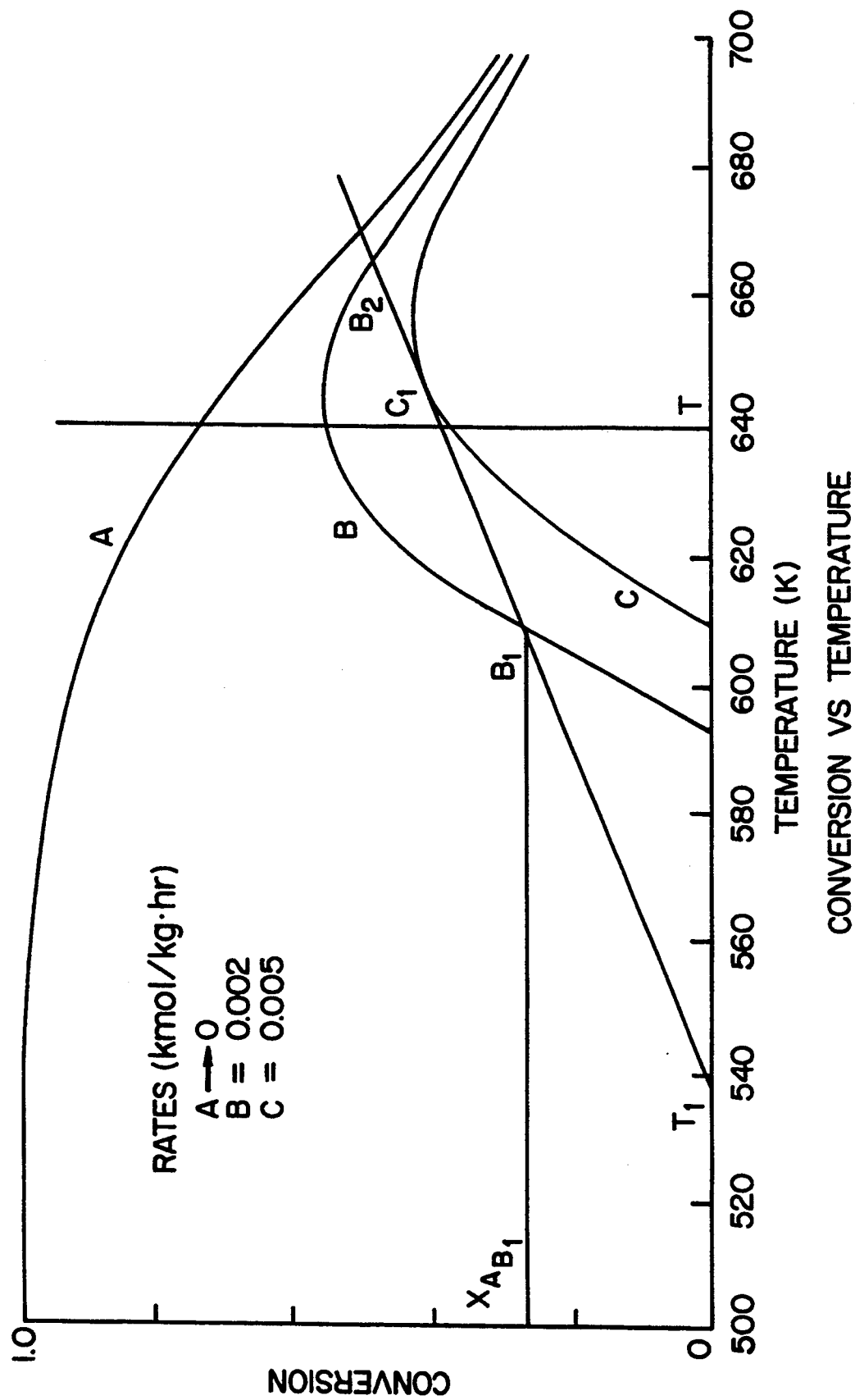
FIG. 1 is a graph showing constant rate curves of methanol formation.

FIG. 1 shows an equilibrium curve for methanol synthesis at 333 atmospheres, two constant rate curves, and an adiabatic operating line, on coordinates showing the fraction converted versus the reaction-system temperature. Curve (A) corresponds to a rate of $10^{-8}$ kmol (kg cat)$^{-1}$h$^{-1}$ and in essence represents the equilibrium for this system. Curve B corresponds to a rate of $2\times10^{-3}$ kmol (kg cat)$^{-1}$h$^{-1}$, and, curve C corresponds to a rate of to $5\times10^{-3}$ kmol (kg cat)$^{-1}$h$^{-1}$. The feed composition has $CO:H_2:N_2:He:CO_2$ in the ratio 1:5:1:2:1 at 333 atmospheres. The curves here and in the other figures were obtained using RESIM, an adiabatic reactor simulation program for the PC which uses the kinetics and parameters quoted by Capelli et al in "Mathematical Model for Simulating Behavior of Fauser-Montecatini Industrial Reactors for Methanol Synthesis", I. & EC. Proc. Des. Dev. II(2), (1972) p. 184–190. These data were obtained using established kinetics. An adiabatic reactor whose feed enters at the temperature where the operating line crosses $X_A=0$ will yield an output at steady state which will invariably fall on this operating line. Exactly how far up this line the output will fall depends on the space velocity used. In the ideal case, all features of FIG. 1 are fixed for each pressure, catalyst, and feed composition including changes in inerts.

The equation of the operating line in this simplest case is:

$$X_A = C_p T / -H_r \tag{1}$$

Thus, $X_A$ is directly proportional to T. This is true in systems which do not have significant secondary reactions or parallel reactions of different orders and do not lose heat to the reactor components or the surroundings. The matter becomes somewhat more complicated in the real world when the reactor and catalyst have finite heat capacities and heat loss may be unavoidable. In that case, the basic heat balance equation becomes:

heat input = heat output +
heat generated by reaction +
heat accumulated in the reactor +
heat lost to surroundings Because a scanning reactor will be examined, which operates in a transient or non-steady state mode, the accumulation term cannot be ignored. By convention, the input condition is the enthalpy datum: i.e. heat input=0.

The heat output term will depend on the composition of the products and can be written:

heat output = $C_p(T_o-T_i d_i)(1-X_A) + C_{pp1}(T_o-T_i)(X_A-X_p)(X_A-X_p) + C_{pp2}(T_o-T_iX_p)$ where only one primary product p1 and one secondary product p2 are postulated. More complex systems can be envisioned without changing the overall conclusions.

In accounting for heats of reaction, the heat of conversion of reactant to primary product p1 and the heat of conversion of that product to the secondary product p2 must be considered:

heat generation by reaction = $H_{ri}X_A + H_{pi}X_p$ where $X_p$ is the fraction of conversion of the reactant A to secondary products p2 while $X_A$ is the total fraction of reactant A converted. The subscripts ri and pi refer to heats of reaction of the feed A to p1 and p2 at the inlet temperature $T_i$.

In considering the accumulation terms, the heat capacity and mass of each of the components of the reactor must be considered. These will include walls, the catalyst charge and any other items present in the reactor:

$$\text{accumulation} = \sum_s C_{ps} m_m T_s$$

where the term $T_s$ is the temperature difference between the reactor walls etc. and the reactants and the subscript s indicates the component of the reactor. The heat capacity $C_{ps}$ is expressed in units commensurate with those of m, the quantity of a solid component in the reactor. Since at the beginning of a temperature scan the reactor is all at $T_i$, $T_s$ is a function of both time and position in the reactor.

Finally, heat losses from the reactor will take the form:

$$\text{heat loss} = \sum_f h_f S_{2f} T_f$$

where h is the heat transfer coefficient, s is the heat transfer surface and $T_f$ is the driving force due to temperature difference between the reactor component f and its surroundings. Again, $T_f$ will be a function of time. These terms are collected to present a more complete form of equation 1

$$X_A = \frac{C_p T + {}_s H_{p2} X_p + \sum_f m_s C_{ps} T_s + \Sigma h_f S_f T_f}{-H_{r2}} \quad 1(a)$$

It can be seen that Equation 1a reduces to Equation 1 when all of the following are true:
a) secondary reaction does not occur and $X_p=0$
b) the heat capacity of the reactor is very small and $C_{ps}\to 0$ or when heat transfer to the reactor material is very slow, or at steady state when $T_s=0$
c) heat loss from the reactor components is small because
1) $h_f$ are all very small
2) $T_f$ is minimized by appropriate instrument design.

Under appropriate conditions, there will exist a unique operating line for every real reactor under a prescribed set of operating conditions and, in the case of the adiabatic reactor, it is obvious that the operating line is unique. The reaction rate curves, on the other hand, are independent of the heat effects and will depend only on temperature, feed composition, catalyst activity and pressure regardless of adiabaticity.

To get from the input condition shown as $T_1$ in FIG. 1 to an output condition at $B_1$ using a plug flow reactor (PFR) will require a certain space time $\tau_{B1}$. To reach condition $C_1$ from $T_1$ will require a different space time $\tau_{C1}>\tau_{B1}$, etc. In a PFR, each point on the operating line is reached at a unique space time.

At the space velocity which results in $\tau_{B1}$, an output conversion $X_{AB1}$ will be achieved which will be changing at a rate corresponding to constant rate curve B, regardless of how this point is reached, either along an ideal operating line given by equation 1 or along a more complicated path given by equation 1a or its elaborations. If space velocity is decreased, i.e. increase $\tau$ to $\tau_{C1}$, condition $C_1$ will be reached which is the maximum rate achievable on the operating line starting at $T_1$ and lies on constant rate curve C. Further increases in $\tau$ will result in higher conversions but at decreasing rates. On the way to equilibrium conversion on Curve A, curve B will be encountered again at condition $B_2$. The rate at $B_1$ and $B_2$ will be the same; at $B_1$ it will occur at low conversion and low temperature while at $B_2$ it will take place at high conversion and high temperature. It is clear therefore, that the reactor can be operating at $B_1$ or $B_2$ under steady or non-steady state conditions, and it is apparent that the temperature profile along the length of the reactor, before the condition at $B_1$ or $B_2$ is reached, need not be the same as that which would result if input temperature was constant. It will be appreciated that, in contrast, a steady state condition is one which would eventually be reached at a sufficiently long time from the beginning of the observation if the input temperature, composition etc. is maintained at a constant value. If this constant value is changed, a finite amount of time must elapse before a new steady state is achieved. Nevertheless, at each instant during the transient the instantaneous rate of reaction of a system at point $B_1$ or $B_2$ is defined by the temperature and conversion alone. That condition is completely independent of the conditions along the reactor preceding or succeeding that condition and hence is independent of whether the system as a whole is at steady state or not.

Figure 2:
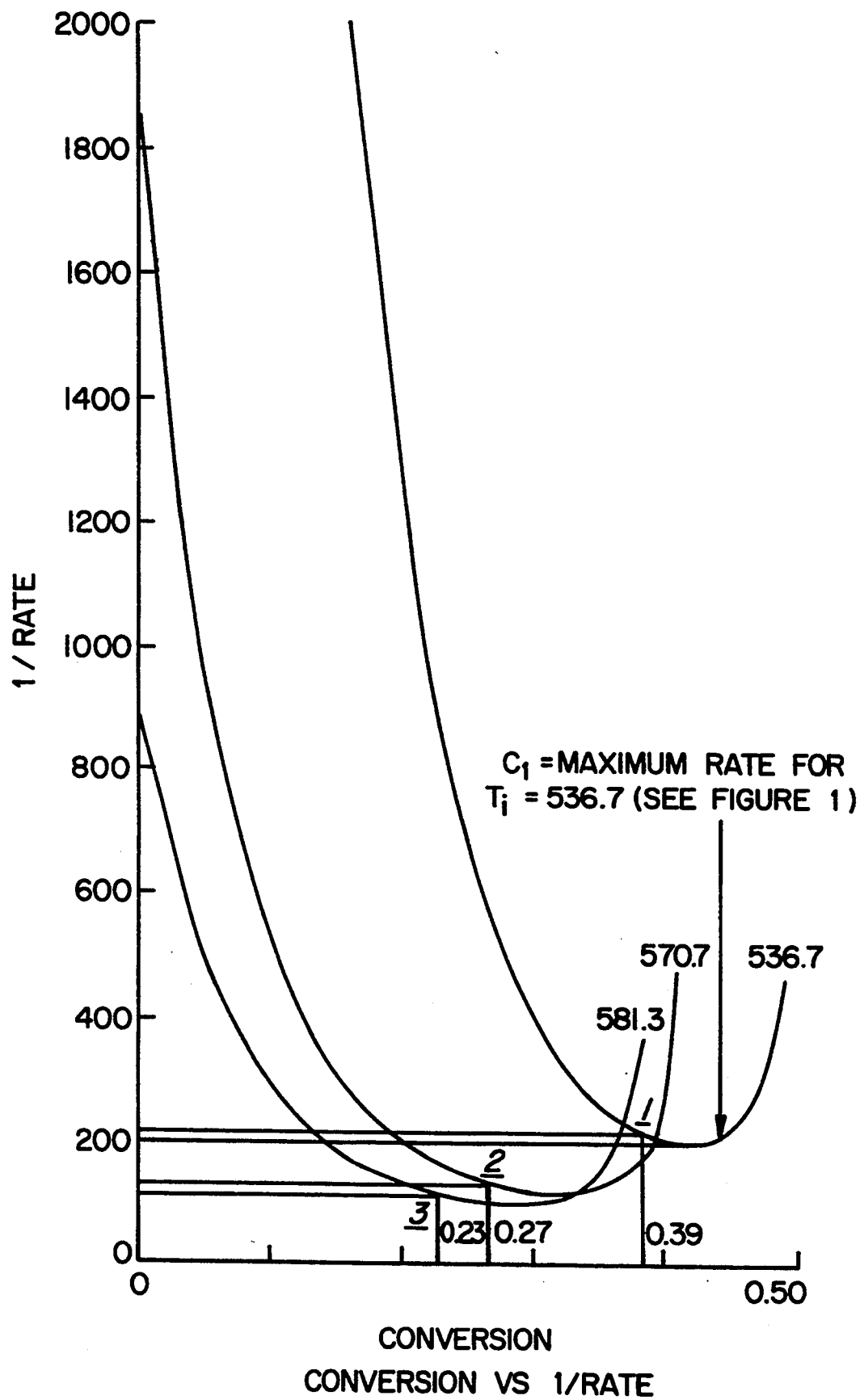
FIG. 2 is a graph showing methanol conversion versus rate$^{-1}$.

FIG. 2 shows a plot of the reciprocal rate versus conversion. From reactor design, theory, this information is used to size the reactor using the general equation:

$$\tau = C_{A0} \int_O^{X_{Af}} dX_A/-r_A \tag{2}$$

The area under the curve on FIG. 2 between $X_A=0$ and $X_A=X_{Af}$ is $$\int_O^{X_{Af}} dX_A/-r_A = \tau/C_{A0} \tag{3}$$

Equation 3 is valid whether the temperature of the system is constant or not. At constant temperature T:

$$dX_A/-r_A|_T = d\tau/C_{A0}|_T \tag{4}$$

or rearranging $$C_{A0} dX_A/d\tau|_T = -r_A|_T \tag{5}$$

In order to obtain the rate at a given reaction temperature;, the value of $dX_A/d\tau$ at that temperature is required. This information is routinely obtained in isothermal reactors by incrementing space velocity in successive runs, however, in TS-PFRs, it may be most readily obtained, not by the procedure of incrementing the input space velocity, but by the simple procedure of ramping the input temperature at constant space velocity and composition, so as to scan an input temperature range from $T_{min}$ to $T_{max}$ and observing the conversion $X_A$ and temperature $T_o$ at the outlet of the reactor at each instant during the scan.

Figure 3:
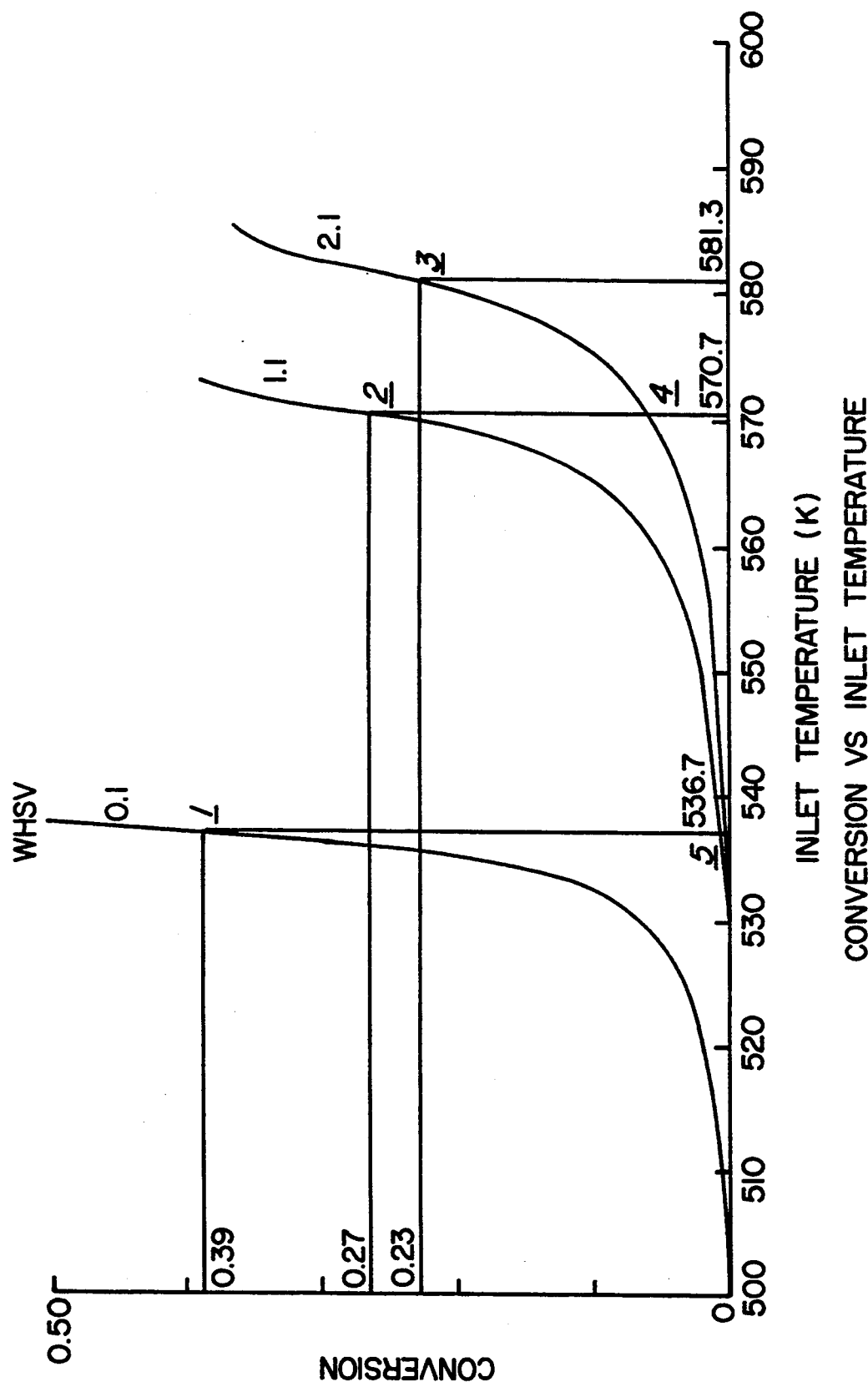
FIG. 3 is a graph showing methanol conversion versus input temperature $T_i$ at three constant space velocities or space times; WHSV=0.1 ($\tau$=10); WHSV=1.1 ($\tau$=0.91) and WHSV=2.1 ($\tau$=0.48)
Figure 8:
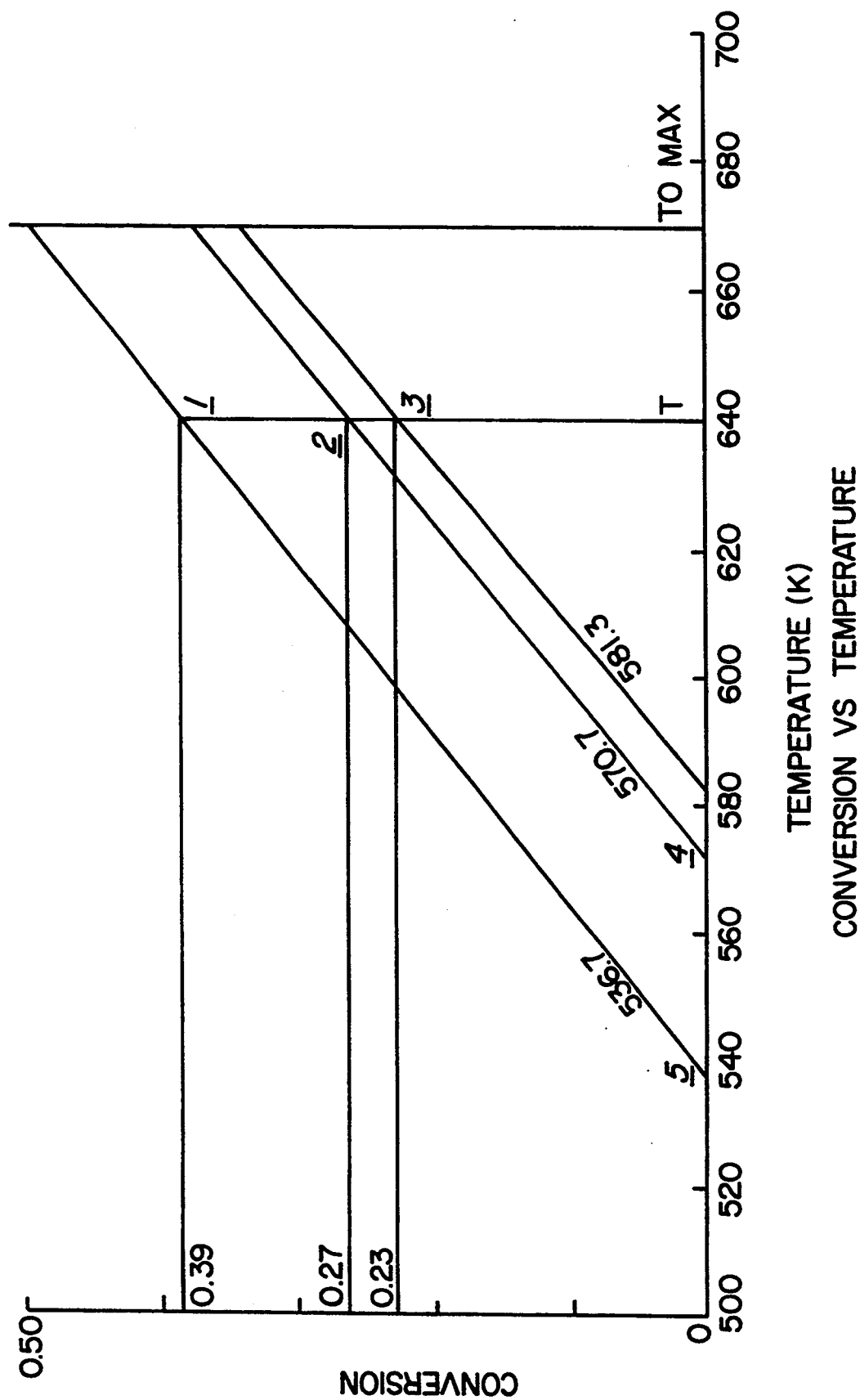
FIG. 8 is a graph of methanol conversion versus temperature for the initial temperatures $T_1=536.7°$ K., $T_2=570.7°$ K. determined in FIG. 3.

The temperature scanning procedure is equivalent to investigating the output condition, at constant $\tau$, on a succession of operating lines, as identified for the 2.1 WHSV curve on FIGS. 3 and 8 by points 3, 4, and 5. In FIG. 3a series of curves showing how $X_A$ varies with the input temperature $(T_i)$ as a result of scans for various constant values of $\tau$, all at constant composition and pressure are shown. In practise, the input temperature is ramped until a preset maximum output temperature $T_{omax}$ is recorded, to protect the reactor or the catalyst or simply to avoid reaching equilibrium conversion. After each scan, a data set consisting of triplets of readings of $T_i$, $T_o$ and $X_A$ at corresponding times during the scan is collected.

Figure 4:
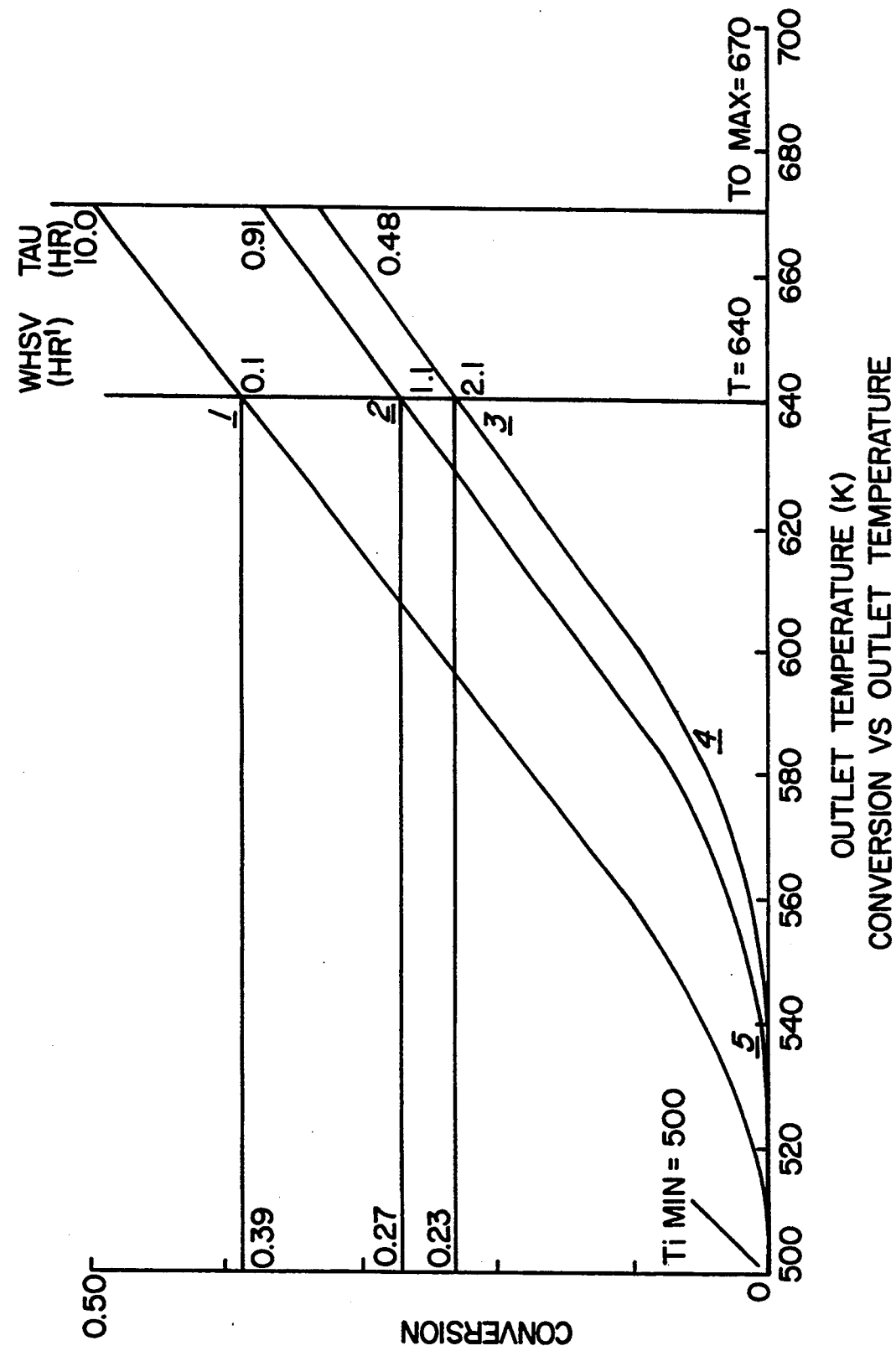
FIG. 4 is a graph showing methanol conversion versus output temperature $T_o$ at the same space velocities as in FIG. 3.
Figure 5:
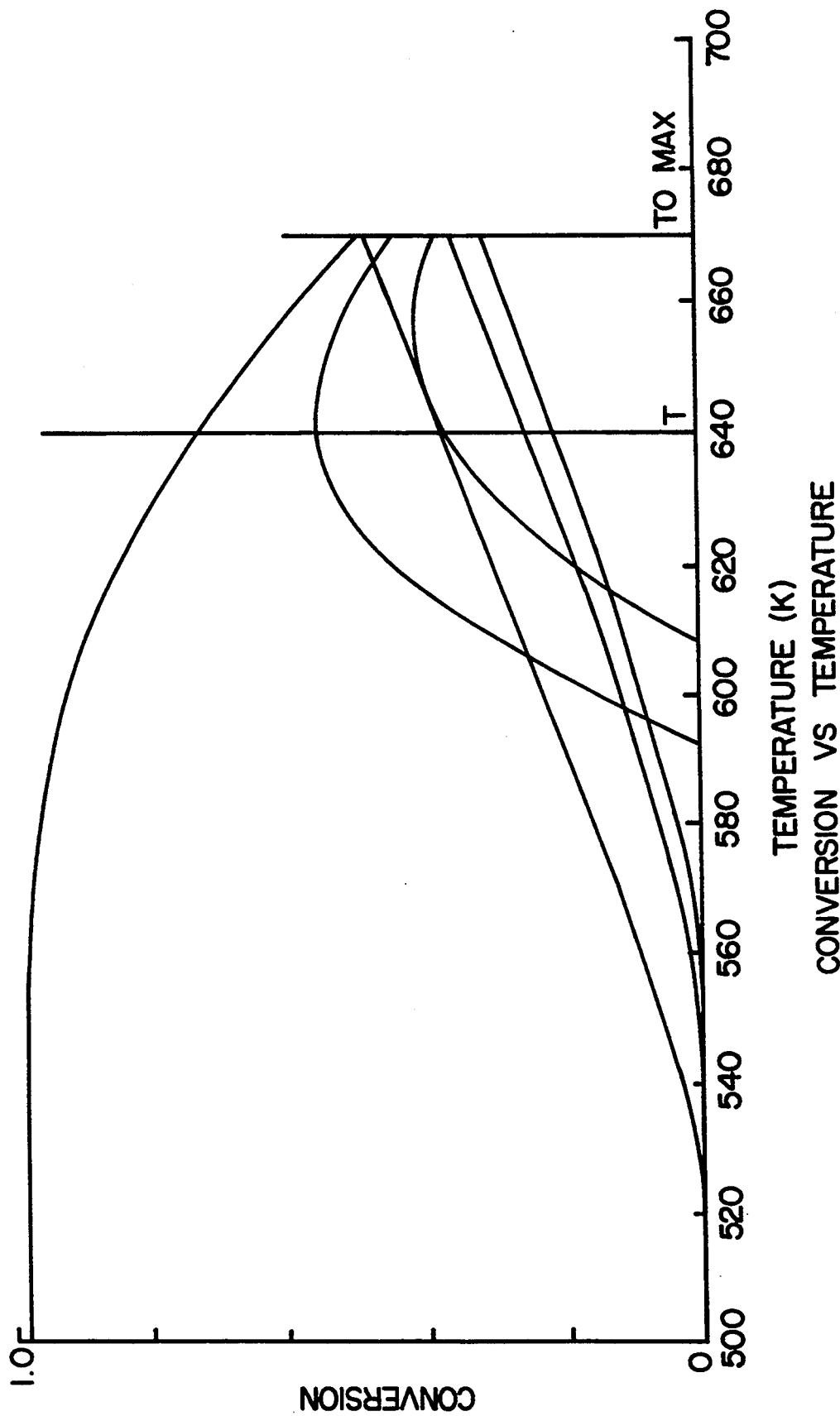
FIG. 5 are conversion curves $X_A$ versus output temperature $T_o$ at constant space time $\tau$ but varying input temperatures $T_i$ superimposed on the equilibrium curve for the system.

Such a data set was used to produce FIG. 3 and can also be plotted in another form by plotting $X_A$ versus $T_o$ as shown in FIG. 4. There is little point in pushing the inlet temperature too high as can be seen by superimposing FIG. 4 on the rate curves of FIG. 1 as shown in FIG. 5. At input temperatures above a certain value, the equilibrium condition at the output, as indicated by the uppermost curve corresponding to WHSV=0.1 is obtained. To investigate the kinetics of a reaction it is preferable to stay below, in fact well away from equilibriums.

Figure 6:
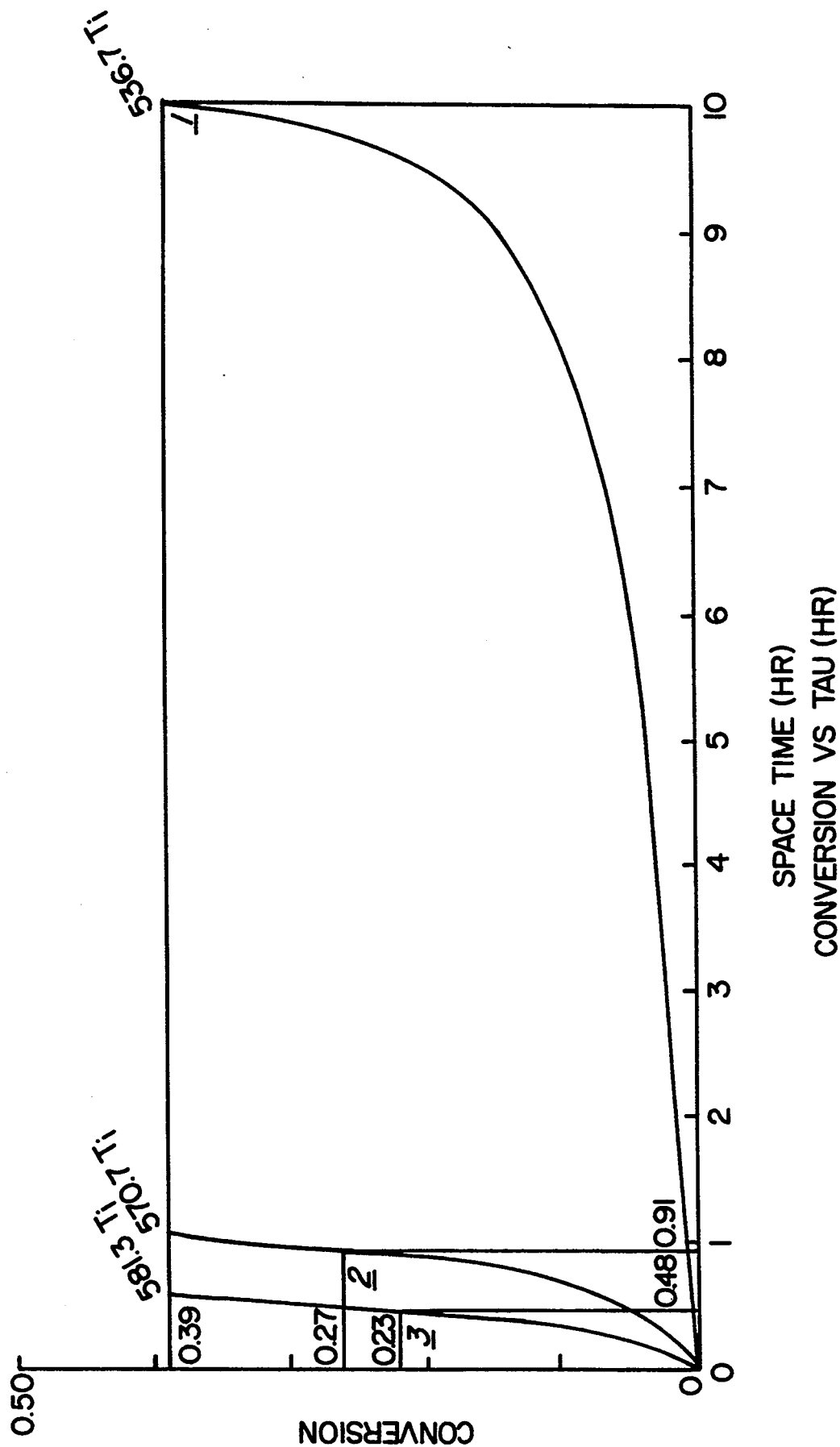
FIG. 6 is a graph showing methanol conversion versus rate constant input temperatures $T_i$ $$T_1=536.7° K., T_2=570.7° K. \text{ and } T_3=581.3° K.;$$

In FIG. 3, it can be seen that at any $T_i$ values of $X_A$ at as many values of $r$ as have been investigated can be obtained. In fact, many sets of such values at various inlet temperatures $T_i$, within the range of temperature studied can be obtained. Each such set can then be plotted as shown in FIG. 6. The curves on FIG. 6 are curves of conversion vs space time along operating lines starting at the various temperatures indicated. Differentiating the curves on FIG. 6 produces $dX_A/d\tau$ at constant $T_i$ and the information necessary to plot FIG. 2. These are the rates which might be observed along an operating line starting at a given $T_i$ if such a measurement were possible. The functional form of the operating line does not matter, as long as there exists a unique operating line for the conditions used.

From a family of curves such as those shown on FIG. 2, the constant rate curves shown on FIG. 1 can be constructed and hence all the information necessary for kinetic model fitting can be obtained. Experimental operating lines which can be used to evaluate the heat effects involved in the reaction can also be generated. For each $X_A$ and $T_i$ from FIG. 3, at $T_o$ can be read off, for the same $r$, on FIG. 4. These give a set of values of $X_A$ and $T_o$ at constant $T_i$. This data, when plotted as $X_A$ vs $T_o$, will produce an experimental operating line.

If the experimental operating lines are almost straight, it can be assumed that the reaction products either are stable or do not have a significant heat of reaction during conversion to secondary products and that the heat loss and accumulation terms in equation 1a are unimportant. If the primary products react to secondary products endothermally, the operating lines will be concave or tend to curl up. Large temperature effects in the heat capacities of products and reactants can also induce curvature in the operating lines. Other effects, such as heat transfer from the reactants to the catalyst or other materials in the reactor, will also induce a concave curvature of the operating lines in ways which in some cases can be quantified. Careful determination of reactor and catalyst heat capacities, of the heats of reaction for secondary reactions and minimization of heat loss in order to approach adiabatic conditions, can be used to derive a fuller description of the observed operating lines. The time-dependent terms of Equation 1a can also be evaluated by suitable instrument calibration procedures.

Even if nothing of the chemistry, thermodynamics or kinetics of the reaction is known, useful qualitative information about the reaction from data such as that shown in FIG. 3 can be obtained. A Temperature Scanning Reactor (TSR) run plotted on the coordinates of FIG. 3, when repeated on a different catalyst formulation, will show if the new catalyst is more active. The curves for the more active catalyst would lie above those for the less active. There is nothing to prevent two such curves, obtained on different catalysts, from crossing. This would simply indicate that the activation energies or mechanisms of reaction are different on the two catalysts, thereby providing additional useful information.

Experimental Procedure

Figure 9:
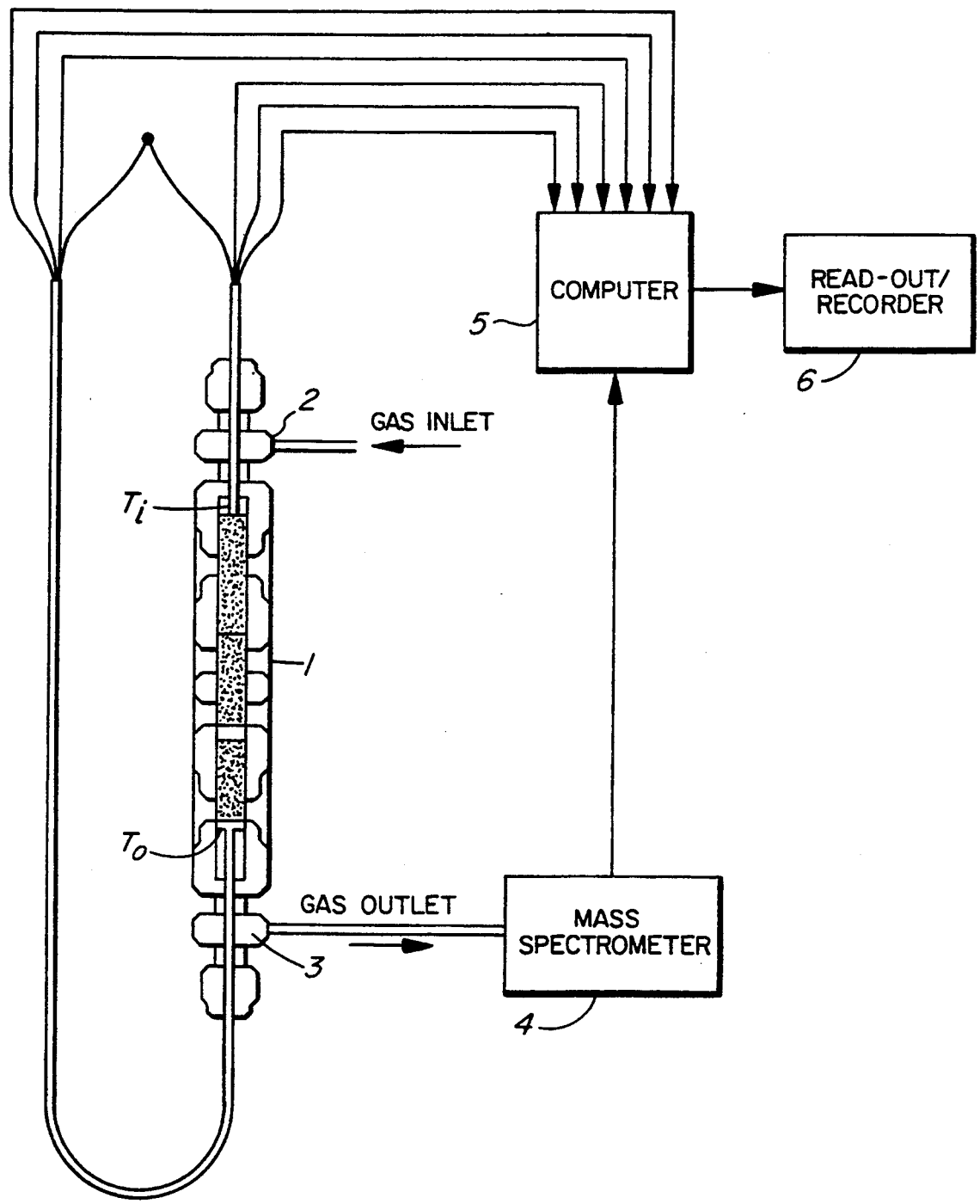
FIG. 9 is a schematic diagram of a temperature scanning reactor used in the present invention.

An automated temperature scanning reactor 1 apparatus, as seen in FIG. 9, can be set up in such a way that feed space velocity is maintained at a constant value, while reactant input temperature $T_i$ at gas inlet 2 is ramped over a range of temperatures ending at some input temperature which results in a maximum allowed output temperature $T_{omax}$ at gas outlet 3. The reactor 1 is then cooled, equilibrated at its initial input temperature $T_{imin}$ and a new space velocity selected. The ramping of the temperature is repeated and stopped again when $T_{omax}$ is reached. The procedure is repeated at as many space velocities as necessary, say about 10. The data gathered during each temperature scan consist of a set of $T_i$ and corresponding $T_o$. If necessary, $X_A$ is followed at the same time using on-line FTIR or MS analysis using a mass spectrometer 4 or other analytical facility for continuous monitoring of output conversion. In the best of cases, $X_A$ may be related to T by calculation or by auxiliary experiments.

An experimental setup which approaches an ideal adiabatic reactor is useful for simplifying the measurement of $X_A$. In the ideal case, equation 1 will apply and $X_A$ can be calculated from the difference between $T_o$ and $T_i$. Departures from the adiabatic condition may necessitate the evaluation of the correction terms in equation 1a. If the necessary terms can be quantified, an instantaneous conversion monitoring detector at the outlet of the reactor is unnecessary. Thus a series of temperature scans will yield for each space velocity T a set of data consisting of the triplets $T_i$, $T_o$ and $X_A$.

Figure 7:
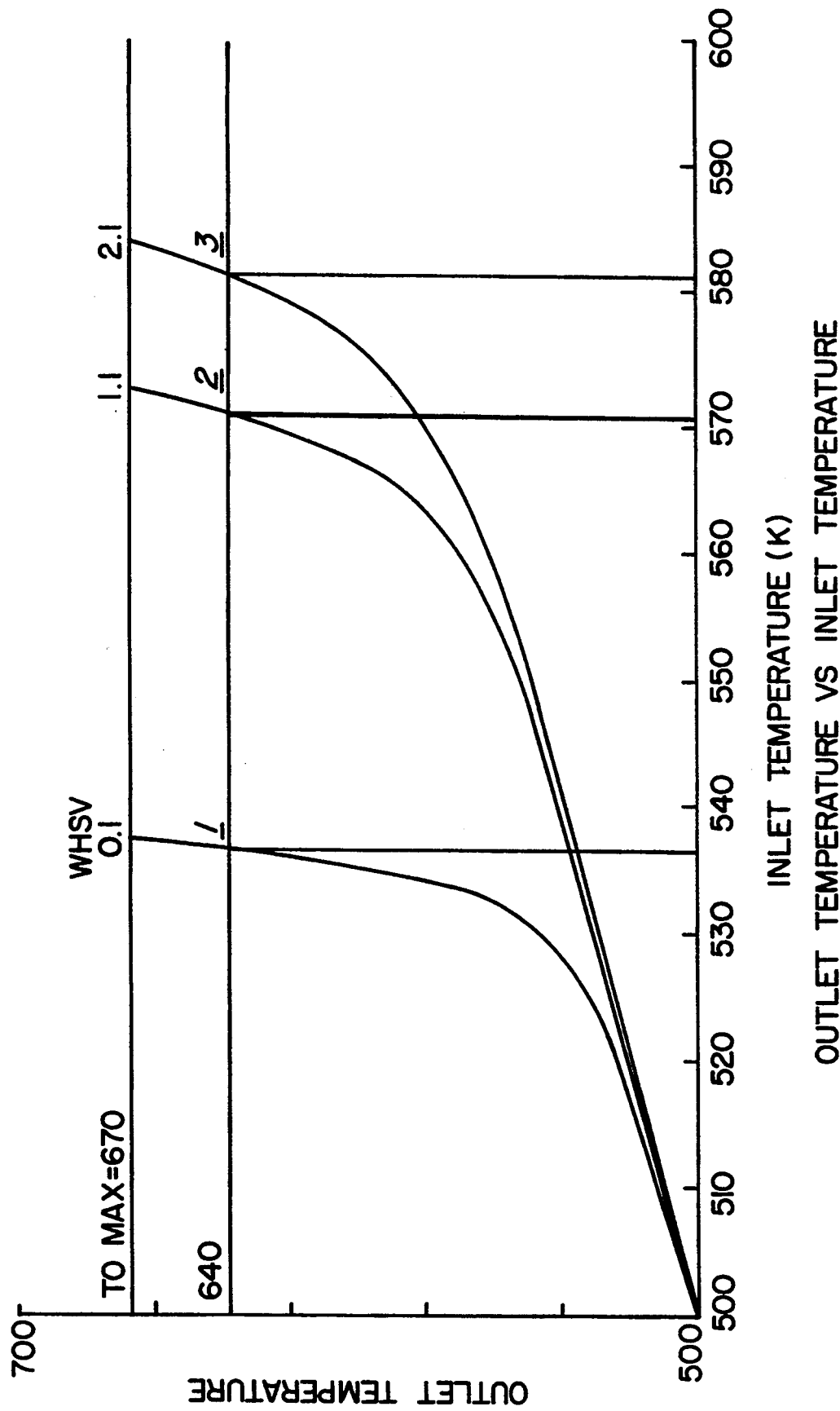
FIG. 7 is a graph of stimulated behavior of output temperature $T_o$ as a function of input temperature in an adiabatic reactor for methanol synthesis operating under the conditions of FIG. 1 at space velocities of FIG. 3.

The data logging, temperature scanning and space velocity changes can all be put under the control of a computer 5. The experimental data consisting of sets of $T_i$ and $T_o$ and $X_A$ at various will be logged numerically or presented graphically on recorder 6 to look like the curves shown in FIG. 3, 4 or 7. These are the raw data presentations.

Using $X_A$ data in the form shown in FIG. 4, one or more output temperatures, at which isothermal rate constants are required are selected. In this example T=640K is selected and it is found that the output conversions which occur at this temperature at the three space velocities of 0.1, 1.1 and 2.1 hr$^{-1}$ are 0.39, 0.27 and 0.23. The corresponding conditions are labeled with circled 1, 2 and 3 for cross reference with other figures. These conversions are used in FIG. 3 to find the input temperatures $T_i$ which lead to these output conditions.

Now, the values for $T_i$ thus determined lie at $X_A=0$ on the operating lines shown on FIG. 8 and $X_A$ values form the FIG. 4 should all occur at 640K on the appropriate operating lines, as they clearly do.

If enough scans at various values of $\tau$ are made it is possible to draw curves such as those shown in FIG. 6 to an arbitrary degree of precision by plotting $X_A$ vs $\tau$ at each $T_i$. FIG. 6 is simply a new representation of the experimental data obtained by remapping the raw data. Differentiating the curves on FIG. 6 produces values for plotting FIG. 2. FIG. 2 is also derived from the experimental data and represents the rates of reaction along operating lines. Because it is necessary to differentiate the data on FIG. 6 to obtain FIG. 2, it is clear that enough runs with appropriate values of to make the numerical differentiation accurate will be required.

All that remains is to read the rates from the appropriate curves on FIG. 2 or from a plot of $X_A$ vs rate for the $X_A$ values at the 640K selected on FIG. 4. This produces a set of rates and corresponding conversions at the selected reaction temperature T=640K. This isothermal rate data can be treated in a conventional fashion by fitting it to postulated kinetic models using graphical or statistical methods.

If the feed contains more than one component, this procedure should be repeated at a number of feed compositions in order to determine the kinetic effect of each component in the system. This can be automated and need not complicate data gathering or interpretation beyond what is described above.

Data Handling Formalism

All of the above can be readily programmed on a computer by applying the following transformations of the basic $T_i$, $T_o$ and $X_A$ data set.

Let
$T_i(i)$ be the set of input temperatures with i=1 to m
$\tau(j)$ be the set of space times (or 1/WHSV) with j=1 to n
$T_o(i,j)$ be the set of output temperatures
$X_A(i,j)$ be the set of output conversions.

In practice the set of input and output temperatures will be dense, and linear interpolations between adjacent measured results in the i direction can be applied. The space velocity set will, for reasons of economy of effort, be much sparser and necessitate second order interpolations.

When the rate of reaction is considered, and if the data in the j direction are sparse, a quadratic interpolation might be used:

$$-r(i,j) = C_{A0}\left[ \frac{X(i,j) - X(i,j-1)}{\tau_j - \tau_{j-1}} + \right.$$

$$\left. \frac{X(i,j+1) - (i,j)}{\tau_{j+1} - \tau_j} - \frac{X(i,j+1) - X(i,j-1)}{\tau_{j+1} - \tau_{j-1}} \right] \quad (7)$$

for all j=2, ..., n−1 while for the end members of the set $$-r(i,1) = C_{A0}\left[ \frac{X(i,2) - X(i,1)}{\tau_2 - \tau_1} + \right.$$

$$\left. \frac{X(i,3) - X(i,1)}{\tau_3 - \tau_1} - \frac{X(i,3) - X(i,2)}{\tau_3 - \tau_2} \right] \quad (8)$$

and $$-r(i,n) = C_{A0}\left[ \frac{X(i,n) - X(i,n-1)}{\tau_n - \tau_{n-1}} + \right.$$

$$\left. \frac{X(i,n) - X(i,n-1)}{\tau_n - \tau_{n-2}} - \frac{X(i,n-1) - X(i,n-2)}{\tau_3 - \tau_2} \right] \quad (9)$$

In the above, $C_{A0}$ is the initial feed concentration of the base component A whose conversion we are tracking. The formulas can be simplified somewhat by carrying out the experimental program so that for all j the step size in space time is the same:

$$\tau_j - \tau_{j-1} = \text{constant} \quad (10)$$

Alternately spline functions may be fitted and differentiated directly.

A complete table of rates $r(i,j)$ can therefore be assembled in one-to-one correspondence with the measurements of $T_o$ and $X_A$. This can then be used in a program which simultaneously evaluates all rate constants and their Arrhenius parameters.

If the density in the i direction is high, rates at any desired temperature can be interpolated within the range of the scan by linear interpolation and rate constants at selected isothermal conditions can be evaluated. In the linear case, an output temperature $T_o(k,j)$ such that k is constant for all j is selected. Output temperatures which bracket the desired $T_o$ at each $r$ are identified. Let these output temperatures be:

lower value = $T_o(1,j)$ higher value = $T_o(h,j)$ where 1 and h correspond to actually measured values of $T_o$ at conditions 1 and h. Each of these conditions has a corresponding rate $r(1,j)$ and $r(h,j)$. These can be linearly interpolated to give the new rates at k enlarging the set of available temperature conditions to m+1:

$$-r(k,j) = r(1,j) + \frac{T_o(k,j) - T_o(1,j)}{T_o(h,j) - T_o(1,j)} [r(h,j) - r(1,j)] \quad (11)$$

The corresponding conversion is:

$$X_A(k,j) = X_A(1,j) + \frac{T_o(k,j) - T_o(1,j)}{T_o(h,j) - T_o(1,j)} [X_A(h,j) - X_A(1,j)] \quad (12)$$

In this way, a set of $r(k,j)$ and corresponding $X_A(k,j)$ values is calculated. Such sets of isothermal rates and corresponding conversions can be obtained at many temperatures. They can be processed further by well-known means to determine the best kinetic expression and its parameters using model discrimination techniques or, in cases when the rate expression is known, to produce rate parameters, activation energies, etc. As FIG. 6 makes plain, the important experimental requirement is that enough space velocities must be used to define the curves of $X_A$ versus $r$ in sufficient detail so that equations 8-10, or other fitting procedures, are applicable within tolerable limits. The policy of keeping $(\tau_j - \tau_{j-1})$ constant, though it simplifies computation, may require a large number of experiments to determine each $X_A$ versus $r$ curve with adequate precision. In general, it may be best to vary $(\tau_j - \tau_{j-1})$ in order to minimize experimental effort and define each curve in as much detail as is necessary.

If each value of $r$ can be scanned in 30 minutes, and if 10 values of $\tau$ will suffice for a given investigation, and if it takes 30 minutes to reset $T_i$ min and change the space velocity, then a typical completely automated kinetic investigation using the TSAR should produce a best-fit model and its full set of kinetic parameters in something like a 24-hour period of automated data collection.

The data will yield, in principle, an unlimited number of isothermal data sets of rate $r_A$ and conversion $X_A$ between the limits of the scans with something in the order of 10 space velocities at each temperature. This abundance of information, available in 24 hours, should be compared to the small set of data normally generated in months-long kinetic investigations.

It will be appreciated that while this invention has been described with reference to a plug flow reactor (PFR) and particularly an adiabatic plug flow reactor (APFR), the principles thereof are equally applicable to Continuous Stirred Tank Reactors (CSTR) and Batch Reactors.

The operating procedures for the CSTR are the same as for the Plug Flow Reactor i.e. ramping input temperature and recording output temperature and conversion. The equations required to calculate rates from CSTR data are simpler than those described above for the PFR and this alone may make the use of a suitable CSTR preferred in the application of the experimental methods described above. The CSTR has other attractive features such as better temperature control and lack of thermal gradients which may make its application even more attractive.

In the case of Batch Reactors it is possible to maintain uniform temperature in the reactor while ramping the temperature over a selected range. The advantage of this type of reactor is that high pressure reactions or the reactions of solids may be investigated by ramping the temperature of reactor contents while observing the degree of conversion and the temperature of the contents. This operation is advantageous in cases where kinetics are at present being studied in batch autoclaves or in atmospheric pressure batch reactors.

The rate of data acquisition can be doubled over and above that available by means of the procedures described above by the simple expedient of ramping the temperature up to a selected limit at a fixed space velocity and, instead of cooling back to the initial condition before the next data acquisition run, proceeding to change the space velocity at the high temperature limit and cooling the reactor with feed being supplied at the new space velocity. Data can then be acquired both on the temperature up-ramp and on the down-ramp. The space velocity is once again changed at the bottom of the ramp and a new up-ramp initiated. In this procedure there is essentially no "idle time" for the reactor and productivity of the apparatus is maximized.

Note also that the methods outlined in the above are applicable with minor alterations to cases where the reactor is not operated in an adiabatic manner, cases where the volume of the reacting mixture changes due to conversion and a number of other complications which are known to occur in such systems.

We claim:

1. A method for rapid collection of kinetic rate data from a temperature scanning reactor in which a feed stock is reacted under non steady state conditions to form a conversion product comprising,
   ramping the input temperature of said feed stock rapidly over a selected range of temperature,
   continuously monitoring output conversion and output temperature while ramping the input temperature and determining a rate of reaction which is representative of steady-state conditions from input and output temperature and output conversion data obtained during said non-steady state operation of the reactor.

2. A method as claimed in claim 1 wherein said reactor is selected from the group consisting of a plug flow, continuous stirred tank, and batch reactors.

3. A method as claimed in claim 2 wherein said reactor is operated in a non-adiabatic mode.

4. A method as claimed in claim 2 wherein said reactor is operated in an adiabatic mode.

* * * * *

UNITED STATES PATENT AND TRADEMARK OFFICE
CERTIFICATE OF CORRECTION

PATENT NO. : 5,340,745
DATED : August 23, 1994
INVENTOR(S) : Bohdan W. Wojciechowski and Norman N. Rice It is certified that error appears in the above-identified patent and that said Letters Patent is hereby corrected as shown below:

At col 10 line 53 after "ture" insert ","

Signed and Sealed this

Twenty-first Day of October 1997

Attest:

BRUCE LEHMAN

Attesting Officer          Commissioner of Patents and Trademarks